United States Patent [19]

Evans

[11] Patent Number: 4,481,213

[45] Date of Patent: Nov. 6, 1984

[54] 4-HALOALKYLAMINO SUBSTITUTED CHROMANOL USEFUL AS ANTIHYPERTENSIVE AGENT

[75] Inventor: John M. Evans, Roydon, England

[73] Assignee: Beecham Group Limited, England

[21] Appl. No.: 398,553

[22] Filed: Jul. 15, 1982

Related U.S. Application Data

[63] Continuation of Ser. No. 295,134, Aug. 21, 1981, abandoned.

[30] Foreign Application Priority Data

Aug. 21, 1980 [GB] United Kingdom ............... 8027204

[51] Int. Cl.³ ..................... A61K 31/35; C07D 311/02
[52] U.S. Cl. ..................................... 424/283; 549/399
[58] Field of Search ........................ 549/399; 424/283

[56] References Cited

U.S. PATENT DOCUMENTS

| 4,048,317 | 9/1977 | Watts | 549/399 |
| 4,119,643 | 10/1978 | Watts | 549/399 |
| 4,203,895 | 5/1980 | Parcell et al. | 549/399 |
| 4,251,537 | 2/1981 | Evans | 549/399 |

FOREIGN PATENT DOCUMENTS

| 1511187 | 3/1977 | United Kingdom | 549/399 |
| 1495526 | 12/1977 | United Kingdom | 549/399 |
| 1509853 | 5/1978 | United Kingdom | 549/399 |

OTHER PUBLICATIONS

Chem. Abstract, vol. 84, p. 492, 84:1.35572t (1976).

Primary Examiner—Nicky Chan
Attorney, Agent, or Firm—Jacobs & Jacobs

[57] ABSTRACT

A compound of the formula (I):

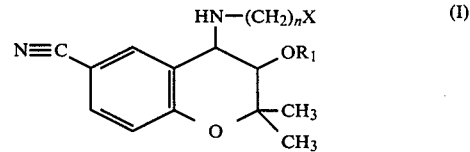

and pharmaceutically acceptable salts thereof wherein $R_1$ is hydrogen or $C_{1-6}$ alkyl or an acyl group of 1 to 8 carbon atoms; n is 2, 3 or 4; X is halogen; and the $OR_1$ and $HN(CH_2)_nX$ moieties are trans; has anti-hypertensive activity and a low level of cardiac side-effects.

8 Claims, No Drawings

4-HALOALKYLAMINO SUBSTITUTED CHROMANOL USEFUL AS ANTIHYPERTENSIVE AGENT

CROSS-REFERENCE

This is a continuation, of Ser. No. 295,134 filed Aug. 21, 1981, abandoned.

This invention relates to novel compounds having anti-hypertensive activity, to a process for their preparation, and to pharmaceutical compositions containing them.

UK Pat. Nos. 1 495 526, 1 509 853 and 1 511 187 disclose various distinct classes of trans-3-hydroxy-4-amino-chroman derivatives as having anti-hypertensive activity.

European patent application No. 79301934.0 (Publication No 0 009 912) discloses compounds of the formula (A):

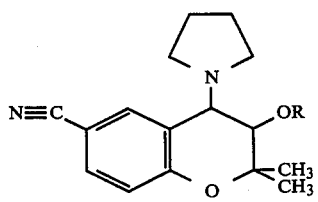

(A)

wherein R is hydrogen, $C_{1-3}$ alkyl, or $C_{1-8}$ acyl, and salts thereof, which also have blood pressure lowering activity but have less unwanted cardiac effects.

A group of compounds, structurally distinct from the compounds referred to above has now been found, which group has useful anti-hypertensive activity and a low level of unwanted cardiac sideeffects.

Accordingly, the present invention provides compounds of the formula (I):

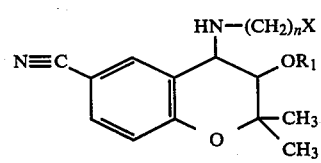

(I)

and pharmaceutically acceptable salts thereof wherein $R_1$ is hydrogen or $C_{1-6}$ alkyl or an acyl group of 1 to 8 carbon atoms; n is 2, 3 or 4; X is halogen; and the $OR_1$ and $HN(CH_2)_nX$ moieties are trans.

Suitable alkyl groups $R_1$ in relation to formula (I) are the methyl, ethyl and n-propyl groups of which the methyl group is most suitable. Suitable acyl groups $R_1$ in relation to formula (I) are unsubstituted carboxylic aryl groups much as unsubstituted aliphatic acyl or benzoyl; and in particular $C_{1-4}$ aryl groups, such as acetyl.

Preferably $R_1$ in relation to formula (I) is a hydrogen atom.

Preferably n is 3.

Suitable halogens X include chlorine and bromine.

Preferably X is chlorine.

The compunds of the invention can exist in optically active forms. Those skilled in the chemical arts will realise that racemic mixtures of the compounds can be separated into pure optical isomers using such techniques as fractional crystallization using optically active acids or the like. All such forms, and mixture thereof, are covered by this invention. It is particularly convenient to prepare and use the compounds of the formula (I) as racemic mixtures.

Suitable acid addition salts of the compounds of the formula (I) are those with pharmaceutically acceptable inorganic or organic acids such as hydrochloric, hydrobromic, phosphoric, sulphuric, methanesulphonic, toluenesulphonic, acetic, propionic, succinic, citric, tartaric, mandelic, lactic, gluconic or the like acid.

The present invention also provides a process for the preparation of a compound of the formula (I) or a pharmaceutically acceptable salt thereof which process comprises the reaction of a compound of the formula (II):

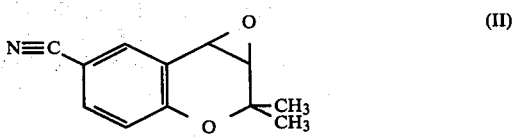

(II)

with a compound of formula $H_2N(CH_2)_nX$ wherein n and X are as hereinbefore defined; or the reaction of a compound of formula (III):

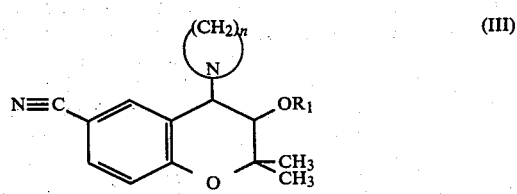

(III)

wherein $R_1$ and n are as hereinbefore defined with an acid HX wherein X is as hereinbefore defined; and thereafter optionally reacting the thus produced compound of the formula (I) wherein $R_1$ is a hydrogen atom to alkylate or acylate said compound, resolving any of said compounds and/or salifying any of the resulting compounds or formula (I). The transisomer is specifically formed.

The reaction of the epoxide (II) with $H_2N(CH_2)_nX$ may be carried out at any non-extreme low, medium or high temperature (for example, $-10°$ C. to $200°$ C.) but in general ambient or slightly elevated temperatures are most suitable (for example $12°$ or $100°$ C.). The reaction is normally carried out in a solvent such as a lower alcohol or lower ketone, for example methanol, ethanol, propanol, acetone or methylethylketone. It has been found that the reaction proceeds smoothly if carried out in refluxing ethanol.

The desired product may be obtained from the reaction mixture by removal of the solvent which is normally accomplished by evaporation under reduced pressure. The initial product any contain some epoxide. This may be separated by dissolving the reaction product in ethyl acetate and extracting into dilute acid. If desired the solvent may be evaporated at this stage but it is usually more convenient to basify, back extract into ethyl acetate and recover by evaporation at reduced pressure. If a salt is desired this product (the free base) may be dissolved in diethyl ether containing a little ethanol and treated with a solution of the acid for example in diethyl ether. The desired salt may then be collected by filtration.

The reaction of the compound of formula (III) with acid, suitably aqueous acid, may be carried out at any non-extreme temperature (for example −10° C. to 150° C.) and suitably at a temperature between 10° C. and 50° C.

The compound of formula (III) may be prepared by the reaction of the compound of formula (II) with a compound of formula

wherein n is as hereinbefore defined. Conditions for this reaction are as hereinbefore described for the reaction of the compound of formula (II) with $H_2N(CH_2)_nX$. Compounds of formula (III) wherein $R_1$ is other than hydrogen may be prepared as hereinafter described for analogous compounds of the formula (I) wherein $R_1$ is other than hydrogen.

The compounds of formula (II) may be prepared as described in U.K. Pat. No. 1511 187 or by analogous methods thereto. Alternatively, the compound of the formula (II) may be prepared and reacted in situ, for example from a corresponding bromohydrin.

Etherification of the initially produced compound of the formula (I) wherein $R_1$ is a hydrogen atom may be effected in conventional manner such as reaction with an alkyl iodide in the presence of a base such as potassium tert-butoxide in an inert solvent such as toluene.

Preparation of esters of the compounds of formula (I) wherein $R_1$ is hydrogen may be by such conventional methods of esterification as reaction with an acylating agent optionally in the presence of an acid acceptor. Suitable acylating agents include acid halides such as a bromide or chloride by reaction with an acid in the presence of a condensation promoting agent such as dicyclohexylcarbodiimide or its chemical equivalent or by reaction with an acid anhydride. Such reactions are generally carried out in a non-hydroxylic solvent of a non-extreme temperature.

Resolution of a compound of the formula (I) may be effected by forming a salt with an optically active acis such as optically active tartaric acid and fractionally crystallising from a suitable solvent such as ethanol.

In a further aspect the product invention also provides a pharmaceutical composition which comprises a compound of this invention and a pharmaceutically acceptable carrier.

The compositions of this invention are most suitably adapted for oral administration although adaptation for other modes of administration such as by injection, for example by intra venous injection for heart failure are also suitable.

In order to obtain consistency of administration it is preferred that the compositions of this invention are in the form of a unit-dose. Suitable unit dose forms include tablets, capsules and powders in sachets or vials. Such unit dose forms aptly contain from 1 to 100 mg of the compound of this invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more aptly from 10 to 100 mg.

Shaped oral dosage compositions are favoured composition aspects.

The compositions of this invention may be formulated in conventional manner, for example in a manner similar to that used for knwon antihypertensive agents such as hydrallazine.

In addition such compositions may contain further active agents such as other anti-hypertensive agents, diuretics and β-blocking agents.

The invention also provides a method of treatment of hypertension, which comprises the administration to the sufferer of an effective amount of a compound of the formula (I) or of a pharmaceutically acceptable salt thereof.

The following Example illustrates the invention.

EXAMPLE

6-Cyano-Trans-4-(3-chloropropylamino)-3,2-dimethyl-2H-benzo[b]pyran-3-ol hydrochloride

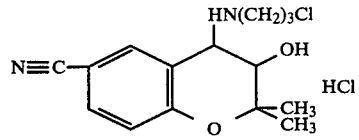

To a stirred solution of chloropropylamine hydrochloride (2.0 g) and sodium hydroxide pellets (0.5 g) in ethanol (150 ml) was added 6-cyano-3,4-epoxy-3,4-dihydro-2,2-dimethyl-2H-benzo[b]pyran (2.0 g, prepared as described in U.K. patent 1,511,187, Example 7). The reaction mixture was stirred at room temperature for 15 days and monitored by TLC. The solution was filtered and evaporated, and the resulting gum (1.74 g) chromatographed on 200 g silica gel with elution by ethyl acetate. The early, chromatographically homogeneous fractions were combined (1.16 g), and, dissolved in the minimum quantity of ethanol required, were treated with ethereal anhydrous HCl to give the title compound as a white powder (0.54 g) of mp 250°-253° C.; NMR (in $DMSOd_6$) δ1.11 (s), 1.45 (s), 2.25 (distorted t, J=5, 5 Hz), 3.08 (br multiplet), 3.76 (t, J=5, 5 Hz overlapped with m, 3H), 4.03 (d, J=9 Hz), 4.46 (d, J=9 Hz), 7.03 (d, J=8 Hz), 7.74 (g, J=8, 2 Hz), 8.47 (d, J=2 Hz). Anal. Calcd. for $C_{15}H_{20}N_2O_2Cl_2$:C, 54.39; H, 6.09; N, 8,46; Cl, 21.41. Found: C, 54.36; H, 6.19; N, 8.33; Cl, 21.50%.

Pharmacological Data

The compound of the Example was tested by oral administration of a dose of 1 mg/kg to a group of 6 spontaneously hypertensive rats.

Systolic blood pressures were recorded by a modification of the tail cuff method described by I. M. Claxton, M. G. Palfreyman, R. H. Poyser and R. L. Whiting, European Journal of Pharmacology, 37, 179 (1976). An oscilloscope of W+W BP recorder, model 8002, was used to display pulses. Prior to all measurements rats were placed in a heated environment (33.5+−0.5° C.) before transfer to a restraining cage. Each determination of blood pressure was the mean of at least 6 readings. Spontaneously hypertensive rats (ages 12-18 weeks) with systolic blood pressures 170 mmHg were considered hypertensive.

| Time post Dose (hrs) | % Change in Systolic Blood Pressure | % Change in Heart Rate |
| --- | --- | --- |
| 1 | −14 ± 7 | −1 ± 8 |

| Time post Dose (hrs) | % Change in Systolic Blood Pressure | % Change in Heart Rate |
| --- | --- | --- |
| 2 | −13 ± 7 | −2 ± 6 |
| 4 | −36 ± 5 | +2 ± 5 |
| 6 | −50 ± 2 | +4 ± 3 |
| 24 | −6 ± 2 | −5 ± 6 |
| Initial values | 209 ± 5 | 480 ± 9 |

Toxicity

No toxic effects were observed in these tests.

I claim:

1. A compound of formula (I):

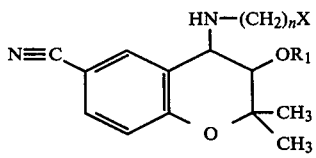

and pharmaceutically acceptable salts thereof wherein $R_1$ is hydrogen or $C_{1-6}$ alkyl or carboxylic acyl of 1 to 8 carbon atoms; n is 2, 3 or 4; X is halogen; and the $OR_1$ and $HN(CH_2)_nX$ moieties are trans.

2. A compound according to claim 1, wherein $R_1$ is hydrogen.

3. A compound according to claim 1, wherein n is 3.

4. A compound according to claim 1, wherein X is chloro.

5. 6-Cyano-trans-4-(3-chloropropylamino)-2,2-dimethyl-2H-benzo[b]pyran-3-ol, or a pharmaceutically acceptable salt thereof.

6. A pharmaceutical composition for the treatment of hypertension, which composition comprises an antihypertensive effective amount of a compound according to claim 1, and a pharmaceutically acceptable carrier.

7. A method of treatment of hypertension, which method comprises the administration to the sufferer of an effective amount of a compound according to claim 1.

8. A compound according to claim 1, which

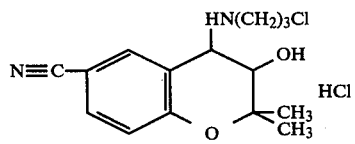

* * * * *